United States Patent [19]

Yokoyama et al.

[11] 3,962,439

[45] June 8, 1976

[54] OXYGEN-TRANSFERABLE EMULSION

[75] Inventors: Kazumasa Yokoyama, Suita; Koichi Yamanouchi, Sakai; Ryoichiro Murashima, Kashihara; Ryozo Watanabe, Takatsuki, all of Japan

[73] Assignee: The Green Cross Corporation, Japan

[22] Filed: Feb. 4, 1974

[21] Appl. No.: 439,638

[30] Foreign Application Priority Data

Oct. 5, 1973  Japan.............................. 48-112047

[52] U.S. Cl................................... 424/248; 424/267; 424/278; 424/283; 424/285; 424/325; 424/342; 424/352

[51] Int. Cl.² .............. A61K 31/535; A61K 31/445; A61K 31/335; A61K 31/35

[58] Field of Search ........... 424/352, 285, 283, 248, 424/267, 325, 278, 342

[56] References Cited
OTHER PUBLICATIONS

Malchesky et al. – Chem. Abst., vol. 74 (1971), p. 51336z.
Watanabe et al. – Chem. Abst., vol. 76 (1972), p. 131465x.
Samejima et al. – Chem. Abst., vol. 78 (1973), p. 71384z.
Samejima et al. – Chem. Abst., vol. 79 (1973), p. 70220b.
Clark et al. – Fed. Proc. vol. 29 (1970), pp. 1764–1766.

*Primary Examiner*—Sam Rosen
*Attorney, Agent, or Firm*—Cushman, Darby & Cushman

[57] ABSTRACT

Oxygen-transferable perfluorocarbon compounds having 9 to 11 carbon atoms such as perfluorodecalin, perfluoro($C_{3-5}$-alkylcyclohexanes), perfluoro($C_{4-6}$-alkyl tetrahydropyrans), perfluoro($C_{5-7}$-alkyltetrahydrofurans), perfluoro($C_{5-7}$-alkylmorpholins) and perfluoro($C_{9-11}$-trialkylamines) are emulsified in a physiologically acceptable aqueous solution such as Ringer's solution by the aid of a phospholipid as emulsifier and a fatty acid of 8 to 22 carbon atoms, alkali metal salt or monoglyceride thereof as emulsifying adjuvant. The emulsion is stable for a considerable period of time and contains particles having a particle size ranging from 0.05 to 0.3 $\mu$. It is usable as a blood substitute or a perfusate for preservation of the internal organs.

19 Claims, No Drawings

OXYGEN-TRANSFERABLE EMULSION

This invention relates to a stable emulsion of oxygen-transferable fluorocarbon compounds, which is used as a blood substitute, and a process for preparing the same.

It has been known, as is generally discussed in Chapter 9 of "Organ Perfusion and Preservation" edited by J. C. Norman and published by Appletan-Century Crafts, New York, 1968, that some kinds of fluorocarbon emulsions have a possibility to be used as a blood substitute, and particularly as an injection-purpose liquid for executing oxygen-transport in place of blood in mammals.

As to the relationship between the toxicity or adverse effect and particle size of the emulsions of various fluorocarbons it is described in Japanese Patent Preliminary Publication No. 22612/73 that test animals whose total blood has been exchanged with the emulsions can not survive unless the emulsions contain any particles having a size of 0.4 $\mu$ or less and their average particle size is 0.2 $\mu$ or less.

In the preparation of stable fluorocarbon emulsions having such a finely divided particle size, difficulties are encountered owing to the large density of fluorocarbons and the large interfacial tension between the fluorocarbon particles and water, which is caused by the extremely small surface tension and poor affinity with other compound of fluorocarbons. Moreover, an emulsifier is not always effective to all of the fluorocarbons to be emulsified but rather specific. This makes the preparation more complicate.

In 1970, R. P. Geyer reported that rats which had their blood totally exchanged with Pluronic-stabilized emulsions of the fluorocarbon FC-43 survived 4–8 hours, the Pluronic being the Trade mark of nonionic surfactant having a chemical structure of polyoxyethylene-polyoxypropylene copolymer having a molecular weight of about 5,000 to about 15,000, sold by Wyandotte Chemical Corp., Wyandotte, Mich., the fluorocarbon FC-43 being the Trade Mark of perfluorotributylamine sold by Minnesota Mining and Manufacturing Co., St. Paul, Minn. The particle size of the emulsion was reported as small as 0.5 to 1 $\mu$ and stable for a long period of time.

However, emulsions having same particle size and stability as in FC-43 can not be obtained by the use of Pluronic in case of other fluorocarbons such as Freon E-4 (Trade Mark of 2-monohydrononacosafluoro-3,6,9,12-tetraoxa-5,8,11-trimethylpentadecan sold by DuPont de Nemours & Company, Wilmington, Del.), the fluorocarbon FX-80 (Trade Mark of perfluorotetrahydrofuran supplied by Minnesota Mining and Manufacturing Co., St. Paul, Minn.), perfluorodecalin and perfluoro(methyldecalin).

As the stabilizer or emulsifier used other than the Pluronic there have been mentioned lecithin or phospholipid which comes from natural sources such as egg yolk and soybean. This kind of emulsifier acts as a universal emulsifier on various fluorocarbons, and gives an emulsion having an average particle size of 0.15 to 0.3 $\mu$ immediately after the preparation of emulsion, and the size can not tolerate the heat-sterilization and storage of the emulsion, which increase the particle size to 0.3 $\mu$ or more.

An object of the present invention is to provide a stable emulsion of fluorocarbons having a particle size of about 0.05 to 0.3 $\mu$.

Other object of the present invention is to provide a stable emulsion of fluorocarbons whose particles are tolerable to heat-sterilization, and the particle size does not inerease to 0.3 $\mu$ or more over a considerable time of storage.

Another object of the present invention is to provide a low toxic fluorocarbon emulsion as a blood substitute.

Other objects and advantages of the present invention will be apparent from the following description.

According to the present invention, there is provided a stable emulsion in a physiologically acceptable aqueous medium, of an oxygen-transferable saturated aliphatic perfluorocarbon compound having 9 to 11 carbon atoms and a particle size of about 0.05 to about 0.3 $\mu$, which comprises said perfluorocarbon compound, a phospholipid as emulsifier and at least one fatty acid compound as emulsifying adjuvant selected from the group consisting of fatty acids having 8 to 22 carbon atoms, physiologically acceptable salts and monoglycerides thereof, the perfluoro carbon compound having at least one alicyclic ring, heterocyclic ring, nitrogen atom or oxygen atom.

After intensive studies on the acute and chronic toxicity of many kinds of fluorocarbon compounds per se as well as the particle size thereof in the emulsion, it has been found that stable emulsions of lower toxic perfluorocarbons are given by emulsifying specific perfluorocarbon compounds with the aid of phospholipid of egg yolk of soybean under the coworking of a small amount of a fatty acid, fatty acid salt and/or fatty acid monoglyceride. The fatty acid should have 8 to 22 carbon atoms.

According to the studies, it has been found that the fluorocarbon FC-43 and Freon E-4 which have most often used in literatures are accumulated in the internal organs such as liver and spleen for a long period of time when administered to test animals, resulting in an adverse effect to the animals. The fluorocarbon FX-80 having a relatively low boiling point gives a remarkable injury to the lung.

The perfluorocarbon compounds used according to this invention are those not giving such adverse effects to the organs or tissues, and are saturated perfluorocarbon compounds having as a whole 9 to 11 carbon atoms some or whole of which form at least one saturated alicyclic ring, heterocyclic ring together with hetero nitrogen atom and/or oxygen atom, aliphatic tertiary amine together with nitrogen atom or aliphatic ether together with oxygen atom or atoms. The compounds have a boiling point ranging from about 140° to about 160°C and an ability to carry oxygen of at least 30% by volume based on the compound and neither accumulation nor adverse effect in the animal tissue are observed when administered as the emulsion according to the invention.

The first group of the perfluorocarbon compounds used in the invention is a perfluorocycloalkane or perfluoro(alkylcycloalkane) which includes, for example, perfluoro ($C_{3-5}$-alkylcyclohexanes) such as perfluoro(methylpropylcyclohexanes), perfluoro (butylcyclohexanes), perfluoro(trimethylcyclohexanes), perfluoro(ethylpropylcyclohexanes) and perfluoro (pentylcyclohexanes); perfluorodecalin and perfluoro (methyldecalines).

The second group is a perfluoro(alkylsaturated-heterocyclic compound) which includes, for example, perfluoro(alkyltetrahydropyrans) such as perfluoro(butyltetrahydropyrans), perfluoro(pentyltetrahydropyrans) and perfluoro(hexyltetrahydropyrans); perfluoro(alkyltetrahydrofurans) such as perfluoro (pentyltetrahydrofurans), perfluoro(hexyltetrahydrofurans) and perfluoro(heptyltetrahydrofurans); perfluoro (N-alkylpiperidines) such as perfluoro(N-pentylpiperidines), perfluoro(N-hexylpiperidines) and perfluoro (N-butylpiperidine); and perfluoro(N-alkylmorpholines) such as perfluoro(N-pentylmorpholines), perfluoro(N-hexylmorpholines) and perfluoro(N-heptylmorpholines).

The third group is a perfluoro(tert-amine) which includes, for examples, perfluoro(diethylhexylamines), perfluoro(dipropylbutylamines) and perfluoro (diethylcyclohexyl amines); an a perfluoro(dioxalkane), that is, perfluoro(alkylene glycol dialkyl ether), such as perfluoro(3,8-dioxa-2,9-dimethyldecane) or perfluoro(tetramethylene glycol diisopropyl ether), perfluoro(3,7-dioxa-2,8-dimethylnonane) or perfluoro (trimethylene glycol diisopropyl ether) and perfluoro (4,6-dioxa-5,5-dimethylnonane) or perfluoro(isopropylene glycol di-n-propyl ether).

These perfluorocarbon compounds are used alone or in a mixture of their isomers, and further of two or more kinds of the compounds. The compounds may be available on market. Alternatively, they may be produced according to the processes described, for example, in the articles of Industrial and Engineering Chemistry, Vol. 39, page 380 (1949), Journal of Chemical Society, 1950, page 3617, and Advance of Fluorine Chemistry, Vol. I, page 129 (1960).

Among the perfluorocarbon compounds mentioned above, the most preferable ones are perfluorodecalin and perfluoro(methyldecalin) owing to their faster excretion from body, ease of the preparation of its emulsion and availability.

The amount present in the emulsion, of the perfluorocarbon compound used is 10 to 40% (W/V). The symbol "% (W/V)" referred to in the specification and claims of this application means the amount proportion of a material by weight (gram) based on 100 ml of the resulting emulsion.

The phospholipid used as emulsifier in the invention is ones commonly used in the art, and those comprising yolk lecithin or soybean lecithin are preferable. The amount present in the emulsion ranges from about 2 to about 6% (W/V), and preferably about 3 to about 4% (W/V).

The fatty acid compound used as emulsifying adjuvant is a fatty acid having 8 to 22 carbon atoms, a physiologically acceptable salt such as sodium or potassium salt or a monoglyceride thereof, which includes, for example, caprylic acid, capric acid, lauric acid, myristic acid, palmitic acid, stearic acid, behenic acid, palmitoleic acid, oleic acid, linoleic acid, arachidonic acid and sodium or potassium salt and monoglyceride thereof. These fatty acid compounds may be used alone or as a mixture of two or more kinds thereof in such a minor amount of 0.001 to 0.1% (W/V). Among these fatty acid compounds, the preferably ones are those having 14 to 20 carbon atoms and their physiologically acceptable salts, and the most preferable are potassium palmitate and sodium oleate taking into consideration of their good solubility and ease of the preparation of the emulsion.

The emulsion of perfluorocarbon compound according to the present invention contains particles of the compound having a size ranging from 0.05 to 0.3 $\mu$ and an average particle size of about 0.1 $\mu$ to about 0.2 $\mu$, and is stable over a long period of time. The particle size herein referred to is measured according to an modification of a centrifugal sedimentation method proposed by T. Fugita, T. Suyama and K. Yokoyama (Europ. Surg. Res., Vol. 3, pages 436–453, 1971).

The stability of the emulsion will be demonstrated hereinafter. The stabilities against sterilization at 100°C for 30 minutes and storage at 4°C, of five preparations of perfluorodecalin emulsion emulsified with egg yolk phospholipid with or without the aid of the emulsifying adjuvant, potassium palmitate or sodium oleate, are summarized in Table 1, the amounts of the materials contained in the emulsions being mentioned in the Table. The preparations contains further 2.5% (W/V) of glycerin in order to render the emulsions isotonic.

Table 1

| Perfluorocarbon | Emulsifier | Emulsifying Adjuvant (% W/V) | Immediately After Preparation | Average Particle Size ($\mu$) Sterilization 100°C, 30 min. | One month After Storage at 4°C | Three months After Storage at 4°C |
|---|---|---|---|---|---|---|
| Perfluorodecalin 25 % (W/V) | Egg Yolk phospholipid 4 % (W/V) | Potassium Palmitate (0.004) | 0.120 | 0.175 | 0.185 | 0.185 |
| | | (0.02) | 0.115 | 0.155 | 0.160 | 0.170 |
| | | Sodium Oleate (0.004) | 0.115 | 0.165 | 0.175 | 0.185 |
| | | (0.02) | 0.105 | 0.140 | 0.150 | 0.155 |
| | | None | 0.155 | 0.225 | 0.381 | >0.4 |

The perfluorocarbon emulsion of the invention has not an average particle size of more than 0.2 $\mu$ and contains no particles having a size of more than 0.3 $\mu$, and hence it is much harmless as compared with ones in literatures. Reviewing the particle distribution, it will be appreciated that about 70 – 80% of particles distribute in the range below 0.2 $\mu$.

The emulsion according to the invention may be isotonic, containing an appropriate amount of sodium chloride, or other elecrolytes including the components in the Ringer's solution or lactated Ringer's solution. For that purpose, the presence of glycerin in an amount of 2.5% (W/V) is most preferable, because glycerin contributes to the stability in addition to the isotonicity of emulsion.

It can be said again that the perfluorocarbon emulsion of the present invention contains very finely divided particles which does not aggregate into coarse particles during the storage of the emulsion for a considerable long time, and hence it can be administered to mammals without harm of tissue due to the aggregation of the particles. Furthermore, the perfluorocarbon compound used in the invention is smoothly excreted through respiration when administered in the form of emulsion, and no accumulation thereof in liver and spleen is observed.

The perfluorocarbon emulsion of the invention is administered intravenously to animals or patient suffering from bleeding, under oxygen circumstance in an amount responding to the bleeding.

Besides the blood substitute for mammals, the emulsion of the present invention can be used as a perfusate for preservation of the internal organs.

The perfluorocarbon emulsion is prepared according to the present invention by homogeneously mixing the phospholipid, the fatty acid compound and the aliphatic perfluorocarbon compound in the physiologically acceptable aqueous medium, all the materials to be mixed beeing defined preveviously, and emulsifying the mixture by injecting it at a temperature of 45° to 55°C through a slit under a pressure of about 100 kg/cm$^2$ to 500 kg/cm$^2$ thereby subjecting to shearing force and mixing action based on a strong velocity gradient, until the desired particle size previously mentioned is obtained.

The homogeneously mixing of the materials used is carried out by the use of a conventional mixer such as homoblender or propeller stirrer. The emulsification of the mixture is attained by means of a high pressure homogenizer, which is a high pressure pump which homogenizes a mixture of two immiscible liquids by injecting through a slit under a high pressure at a very high velocity to give a shear and mixing to the liquids. The typical homogenizer on market is Monton-Gaulin type homogenizer (Trade Mark of this type of homogenizer sold by Monton-Gaulin Manufacturing Co., In. U.S.A.) which has a multiply stage valve in combination of two or more valves each having a spring therein by which the slits are formed.

The mixture is circulated in this type of homogenizer several times under the total pressure of about 500 kg/cm$^2$ thereby to obtain the stable emulsion of the invention. The operating temperature is kept in a range of 45° to 55°C, and preferably 48° to 52°C.

The present invention is further illustrated by the following Examples which should not be construed to limit the invention thereto.

EXAMPLE 1

To 8.5 liter of lactated Ringer's solution were added 400 g of egg yolk phospholipid and 400 mg of sodium palmitate, and the resulting mixture was stirred by a homoblender to obtain a phospholipid dispersion. 2.5 kg of perfluorodecalin was added to the dispersion while vigorously stirring by the homoblender at a room temperature for 30 minutes to obtain a crude emulsion of perfluorodecalin.

The crude emulsion was placed in a tank of laboratory homogenizer (Manton-Gaulin type 15M-8BA) and was emulsified by circulating through the two stage valves under the total pressure of 500 kg/cm$^2$, in which at first the second stage valve was tighten up to maintein a pressure of 100 kg/cm$^2$, thereafter the first stage valve was tighten up untile the total pressure raised to 500 kg/cm$^2$, while keeping the temperature at 50° ± 5°C, untile a stable emulsion was obtained.

The emulsion obtained was sterilized at 100°C for 30 minutes. The amount of perfluorodecalin in the sterilized emulsion was 27.3% (W/V) and all the particles were below 0.3 μ. The average particle size was 0.16 μ. The particle size was not remarkably changed when the vialed emulsion was stored at a temperature of 4°C for 1 month.

The above procedure was repeated with the exception of the use of sodium palmitate. The resulting emulsion contained a considerable amount of particles having a size of above 0.3 μ and a small amount of above 0.4 μ.

The particle size distribution and average size of the two preparations are shown in Table 2.

EXAMPLE 2

A suspension was prepared by mixing 350 g of soybean phospholipid, 1 g of caprylic acid and 7.0 liter of physiological saline solution by means of a propeller stirrer. To the suspension was added 2.5 kg of a mixture of perfluoro(methyldecalin) isomers and the mixture was stirred vigorously with the stirrer to obtain a crude emulsion. The crude emulsion was emulsified in the same manner as described in the preceeding Example 1. A stable emulsion having a concentration of 32.1% (W/V) of the perfluoro(methyldecalin) was obtained.

The average particle size and particle size distribution of the thus obtaind emulsion are shown in Table 2 together with those of the preparation prepared by the same procedure without the use of caprylic acid.

EXAMPLE 3

A 30.2% (W/V) perfluoro(diethylcyclohexylamine) emulsion was prepared in the same procedure as in Example 2 from 50 g of egg yolk phospholipid, 0.2 g of stearic acid monoglyceride, 850 ml of physiological saline solution and 300 g of perfluoro(diethylcyclohexylamine).

The average particle size and particle size distribution of the emulsion are summerized in Table 2 together with those of an emulsion prepared by the same procedure provided that stearic acid monoglyceride was not used.

Table 2

| Example | Perfluoro-carbon | Emulsifier | Emulsifying Adjuvant | Average Particle Size | Particle Size Distribution (%) | | | |
|---|---|---|---|---|---|---|---|---|
| | | | | | <0.1μ | 0.1–0.2μ | 0.2–0.3μ | >0.3μ |
| 1 | Perfluoro-decalin | Egg Yolk Phospholipid | Sodium Palmitate | 0.16μ | 35.2 | 44.7 | 20.1 | 0 |
| | | | None | 0.35μ | 11.2 | 18.3 | 15.5 | 56.0 |
| 2 | Perfluoro-(methyl decalins) | Soybean Phospholipid | Caprylic Acid | 0.16μ | 32.4 | 37.5 | 30.1 | 0 |
| | | | None | 0.37μ | 10.1 | 10.2 | 13.1 | 66.1 |
| 3 | Perfluoro- | Egg Yolk | Stearic | 0.15μ | 33.5 | 46.2 | 20.3 | 0 |

Table 2-continued

| Example | Perfluoro-carbon | Emulsifier | Emulsifying Adjuvant | Average Particle Size | Particle Size Distribution (%) | | | |
|---|---|---|---|---|---|---|---|---|
| | | | | | <0.1μ | 0.1–0.2μ | 0.2–0.3μ | >0.3μ |
| | (diethyl cyclohexyl amine) | Phospholipid | Monoglyceride None | 0.32μ | 16.5 | 18.0 | 17.5 | 48.0 |

EXAMPLE 4

A 26.8% (W/V) perfluorodecalin emulsion was prepared in the same procedure as in Example 1 from 400 g egg of yolk phospholipid, 400 mg of potassium palmitate, 8.5 liter of 2.5% aqueons glycerin solution and 2.5 kg of perfluorodecalin. The average particle size of the resulting emulsion was 0.118 μ, 0.170 μ after sterilization at 100°C for 30 minutes and 0.180 μ after 3 months' storage at 4°C, respectively, and no particles of more than 0.3 μ were contained.

EXAMPLE 5

Example 4 was repeated, provided, that 400 mg of potassium palmitate was replaced by 2 g of sodium oleate. A 27.1% (W/V) perfluorodecalin emulsion was obtained. The average particle size of the resulting emulsion was 0.110 μ, 0.145 μ after sterilization at 100°C for 30 minutes and 0.160 μ after 3 month' storage of the sterilized emulsion, respectively, and no particles of more than 0.3 μ were contained.

What is claimed is:

1. A stable emulsion in a physiologically acceptable aqueous medium of an oxygen-transferable saturated perfluorocarbon compound having 9 to 11 carbon atoms and a particle size of about 0.05 to about 0.3 μ, which comprises said perfluorocarbon compound, a phospholipid as emulsifier, and at least one fatty acid compound as emulsifying adjuvant selected from the group consisting of fatty acids having 8 to 22 carbon atoms, physiologically acceptable salts and monoglycerides thereof, the perfluorocarbon compound being at least one member selected from the group consisting of perfluoro alkylcyclohexane having 3 to 5 carbon atoms in the alkyl, perfluorodecalin, perfluoro methyldecalin, perfluoro alkyltetrahydropyran having 4 to 6 carbon atoms in the alkyl, perfluoro alkyltetrahydrofuran having 5 to 7 carbon atoms in the alkyl, perfluoro alkylpiperidine having 4 to 6 carbon atoms in the alkyl, perfluoro alkylmorpholine having 5 to 7 carbon atoms in the alkyl, perfluoro trialkylamine, perfluoro (diethylcyclohexylamine), or perfluoro (dioxaalkane), said emulsion being suitable for use as a blood substitute.

2. The emulsion according to claim 1 wherein the perfluorocarbon compound is perfluoro alkylcyclohexane having 3 to 5 carbon atoms in the alkyl, perfluorodecalin or perfluoro methyldecalin.

3. The emulsion according to claim 1 wherein the perfluorocarbon compound is perfluoro alkyltetrahydropyran having 4 to 6 carbon atoms in the alkyl, perfluoro alkyltetrahydrofuran having 5 to 7 carbon atoms in the alkyl, alkylpiperidine having 4 to 6 carbon atoms in the alkyl, or perfluoro alkylmorpholine having 5 to 7 carbon in the alkyl.

4. The emulsion according to claim 1, wherein the perfluorocycloalkane is perfluorodecalin or perfluoro (methyldecalin).

5. The emulsion according to claim 2, wherein the perfluorocycloalkane is perfluoro(butylcyclohexane), perfluoro(methylpropylcyclohexane), perfluoro(trimethylcyclohexane), perfluoro(ethylpropylcyclohexane) or perfluoro(pentylcyclohexane).

6. The emulsion according to claim 3, wherein the perfluoro-saturated-heterocyclic compound is perfluoro(butyltetrahydropyran), perfluoro(pentyltetrahydrofuran), perfluoro(hexyltetrahydrofuran), perfluoro(heptyltetrahydrofuran), perfluoro(N-hexylpiperidine), perfluoro(N-butylpiperidine), perfluoro(N-pentylmorpholine), perfluoro(N-hexylmorpholine) or perfluoro(N-heptylmorpholine).

7. The emulsion according to claim 1, wherein the perfluorocarbon compound is a perfluoro trialkylamine, perfluoro (diethylcyclohexylamine) or perfluoro(dioxa-alkane).

8. The emulsion according to claim 7, wherein the perfluorocarbon compound is a perfluoro-tert-amine which is perfluoro(diethylhexylamine), perfluoro(dipropylbutylamine) or perfluoro(diethylcyclohexylamine).

9. The emulsion according to claim 7, wherein the perfluorocarbon compound is a perfluoro(dioxaalkane) which is perfluoro(tetramethylene glycol diisoproyl ether), perfluoro (trimethylene glycol diisopropyl ether) perfluoro(trimethylene glycol diisobutyl ether) or perfluoro(isopropylidene glycol di-n-propyl ether).

10. The emulsion according to claim 1, wherein the physiologically acceptable aqueous medium is an isotonic solution.

11. The emulsion according to clain 10, wherein the isotonic solution is 2.5% by weight aqueous glycerin solution.

12. The emulsion according to claim 1, wherein the amount of the perfluorocarbon compound is 10 to 40% (W/V), that of the phospholipid is 2 to 6% (W/V) and that of the fatty acid compound is 0.001 to 0.1% (W/V).

13. The emulsion according to claim 1, wherein the fatty acid compound is caprylic acid, capric acid, lauric acid, myristic acid, palmitic acid, stearic acid, behenic acid, palmitoleic acid, oleic acid, linoleic acid or arachidonic acid.

14. The emulsion according to claim 1, wherein the fatty acid is an alkali metal salt of a fatty acid selected from caprylic acid, capric acid, lauric acid, myristic acid, palmitic acid, stearic acid, behenic acid, palmitoleic acid, oleic acid, linoleic acid and arachidonic acid.

15. The emulsion according to claim 14, wherein the alkali metal salt of the fatty acid is potassium palmitate.

16. The emulsion according to claim 14, wherein the alkali metal salt of the fatty acid is sodium oleate.

17. The emulsion according to claim 1, wherein the fatty acid compound is monoglyceride of a fatty acid selected from caprylic acid, capric acid, lauric acid, myristic acid, palmitic acid, stearic acid, behenic acid, palmitoleic acid, oleic acid, linoleic acid and arachidonic acid.

18. The emulsion according to claim 1, wherein the phospholipid is egg yolk phospholipid or soybean phospholipid.

19. The emulsion, according to claim 1 wherein the phospholipid is egg yolk phospholipid or soybean phospholipid, the amount of perfluorocarbon compound is 10 to 40% (W/V), the amount of phospholipid is 2 to 6% (W/V) and the amount of the fatty acid compounds is 0.001 to 0.1% (W/V).

* * * * *